United States Patent [19]

Shum

[11] Patent Number: 4,806,701

[45] Date of Patent: Feb. 21, 1989

[54] PROCESS FOR UPGRADING LIGHT PARAFFINS

[75] Inventor: Victor K. Shum, Naperville, Ill.

[73] Assignee: Amoco Corporation, Chicago, Ill.

[21] Appl. No.: 82,083

[22] Filed: Aug. 5, 1987

[51] Int. Cl.⁴ .............................................. C07C 4/52
[52] U.S. Cl. .................................... 585/417; 585/419
[58] Field of Search ............................... 585/417, 419

[56] References Cited

U.S. PATENT DOCUMENTS 4,582,949  4/1986  Kieffer ................................. 585/415
4,585,641  4/1986  Barri et al. ............................ 502/61

OTHER PUBLICATIONS

Csicsery, *Ind. Eng. Chem. Process Des. Dev.*, vol. 18, No. 2, 1971, pp. 191-197.

Primary Examiner—Curtis R. Davis
Attorney, Agent, or Firm—Ekkehard Schoettle; William H. Magidson; Ralph C. Medhurst

[57] ABSTRACT

The present invention relates to a process for producing aromatic compounds from hydrocarbon gas containing paraffinic hydrocarbons under conversion conditions in the presence of a catalyst comprising a gallosilicate molecular sieve, a Group VIII metal component, and a Group IB metal component.

16 Claims, No Drawings

PROCESS FOR UPGRADING LIGHT PARAFFINS

BACKGROUND OF THE INVENTION

The present invention is directed to a process for upgrading light paraffins such as ethane, propane, and butanes. Interest in upgrading these light paraffins has been growing due to recent and anticipated changes in refinery processing schemes which resulted and will result in a greater supply of such light paraffins. These changes include: the higher severity operation of the reforming process in order to maintain a high octane rating in the absence of or reduction of the lead content in gasoline; the lowering of reid vapor pressure (RVP) specifications; the increased use of oxygenates such as methyl tertiary butyl ether (MTBE) and ethanol resulting in the removal of butanes from the gasoline pool; the increased demand for jet fuel necessitating increased gas oil hydrocracking resulting in more light gas production; and the increase in operating temperatures in fluidized catalytic crackers resulting in more light gas production. Thus, there is great incentive to investigate means for converting these materials into more valuable liquids such as transportation fuels or chemical feedstocks.

The upgrading or conversion of light paraffinic gases and synthesis gas has previously been carried out in the presence of gallium-based or gallium-containing catalysts.

U.S. Pat. No. 4,543,347 (Heyward et al.) discloses a catalyst composition suitable for converting synthesis gas to hydrocarbons which is a mixture of zinc oxide and an oxide of at least one metal selected from gallium and iridium, an oxide of at least one additional metal collected from the elements of Group IB, II through V, VIB and VIII including the lanthanides and actinides and a porous crystalline tectometallic silicate.

U.S. Pat. No. 4,490,569 (Chu et al.) discloses a process for converting propane to aromatics over a zinc-gallium zeolite. This zeolite optionally may also contain palladium. More specifically, the catalyst composition used in the instant patent consists essentially of an aluminosilicate having gallium and zinc deposited thereon or an aluminosilicate in which cations have been exchanged with gallium and zinc ions wherein the aluminosilicate is selected from the group known as ZSM-5 type zeolites.

U.S. Pat. No. 4,585,641 (Barri et al.) discloses crystalline gallosilicates which may be impregnated, ion exchanged, admixed, supported or bound for catalyzing a reaction such as alkylation, dealkylation, dehydrocyclodimerization, transalkylation, isomerization, dehydrogenation, hydrogenation, cracking, hydrocracking, cyclization, polymerization, conversion of carbon monoxide and hydrogen mixtures through hydrocarbons and dehydration reaction. The metal compounds which may be used for ion exchange or impregnation may be compounds of any one of the groups of metals belonging to Groups IB, IIB, IIIA, IVA, VA, VIB, VIIB and VIII according to the Periodic Table. Specifically, preferred compounds include copper, silver, zinc, aluminum, gallium, indium, vanadium, lead, antimony, bismuth, chromium, molybdenum, tungsten, manganese, iron, cobalt, nickel, ruthenium, rhodium, palladium, iridium, platinum, radium, thorium and the rare earth metals. Patentees describe their gallosilicate as "Gallo Theta-1" in contradistinction to an MFI-type gallosilicate .hiwch has a substantially different x-ray diffraction pattern.

U.S. Pat. No. 4,350,835 (Chester et al.) relates to a catalytic process for converting gaseous feedstocks containing ethane to liquid aromatics by contacting the feed in the absence of air or oxygen under conversion conditions with a crystalline zeolite catalyst having incorporated therein a minor amount of gallium thereby converting the ethane to aromatics. The gallium.is present in the catalyst as gallium oxide or as gallium ions if cations in the aluminosilicate have been exchanged with gallium ions. The patent further discloses that the original alkaline metal of the zeolite, when it has been synthesized in the alkali metal form, may be converted to the hydrogen form or be replaced by ion exchange with other suitable metal cations of Groups I through VIII of the Periodic Table, including nickel, copper, zinc, palladium, calcium or rare earth metals.

European Patent Application No. 0 107 876 discloses a process for producing an aromatic hydrocarbon mixture from a feedstock containing more than 50 wt.% $C_2$ through $C_4$ paraffins. Specifically, the process is carried out in the presence of crystalline gallium-silicate having a $SiO_2/Ga_2O_3$ molar ratio of 25 to 250 and a $Y_2O_3/Ga_2O_3$ molar ratio lower than 1 where Y can be aluminum, iron, cobalt, or chromium. The disclosure also teaches a two-step silicate treatment comprising a coke deposition and a coke burn-off with an oxygen-containing gas.

European Patent Appliaation No. 0 107 875 similarly discloses a process for producing an aromatic hydrocarbon mixture from a feedstock comprising more than 50 wt.% of $C_2$ through $C_4$ paraffins. This process is carried out in the presence of a crystalline gallium-silicate, having a $SiO_2/Ga_2O_3$ molar ratio of 25 to 100 and a $Y_2O_3/Ga_2O_3$ molar ratio lower than 1 where Y can be aluminum, iron, cobalt, or chromium.

Light paraffinic gases have also been upgraded to liquid aromatics in the presence of crystalline aluminosilicate zeolite catalysts having incorporated therein a minor amount of a metal selected from Groups VIII, IIB, and IB of the Periodic Table. For instance, U.S. Pat. No. 4,120,910 (Chu) discloses copper-zinc-HZSM-5, platinum-HZSM-5, copper-HZSM-5, and zinc-HZSM-5 catalysts suitable for converting a gaseous paraffinic hydrocarbon feed to aromatic compounds.

It has now been discovered that $C_2$ through $C_5$ light paraffins can most effectively be upgraded to aromatics by the catalytic process of the present invention minimizing methane and ethane production while simultaneously minimizing the production of undesirable heavy aromatics such as naphthalenes.

SUMMARY OF THE INVENTION

Briefly stated, in a broad aspect of the present invention, the invention relates to a process for producing aromatic compounds from hydrocarbon gas containing paraffinic hydrocarbons under conversion conditions in the presence of a catalyst comprising a gallosilicate molecular sieve, a Group VIII metal component, and a Group IB metal component.

In another aspect of the present invention, the invention relates to a novel catalyst composition suitable for producing aromatic compounds from. a hydrocarbon gas containing paraffinic hydrocarbons wherein the composition comprises a gallosilicate molecular sieve, a Group VIII metal component, and a Group IB metal component.

DETAILED DESCRIPTION OF THE INVENTION

The present invention deals with the conversion to aromatic compounds of a hydrocarbon gas containing paraffinic hydrocarbons.

A particularly suitable feedstock for use in the present invention contains the $C_2$ through $C_5$ light paraffins where the gas contains at least 50 wt.% of any one or mixture of such paraffins. A preferred feedstock is one which has a high propane content, typically, a liquefied petroleum gas (LPG). In addition to the mentioned paraffins the feedstock may contain other light gases such as methane, ethene, propene, butene, isobutene, butadiene, and paraffins and olefins with five or more carbon atoms per molecule. These feedstock streams are generally available from several sources in the refinery as mentioned above.

The process of the invention provides for the direct conversion of the light paraffinic gases to valuable aromatic hydrocarbons such as benzene, toluene, and xylenes. These aromatics can be used to increase the octane number of gasoline or as raw materials in the petrochemical industry.

The process of the invention selectively provides for a high yield of benzene, toluene, and xylenes in the $C_4+$ product fraction while minimizing the yield of light $C_1$ through $C_2$ gases and $C_9+$ aromatic compounds in the product fraction.

Broadly, the catalyst employed according to the process of the present invention comprises a gallosilicate molecular sieve component, Group VIII metal compound and a Group IB metal component.

The gallosilicate molecular sieve can be prepared using conventional methods known to those skilled in the art. A suitable method is disclosed in European Patent Application NO. 01 107 875 wiich is incorporated herein by reference.

In another method the gallosilicate crystalline molecular sieves of this invention are characterized by the representative X-ray pattern listed in Table 1 below and by the composition formula:

$$0.9 \pm 0.2 M_{2/n}O: Ga_2O_3: ySiO_2:zH_2O$$

wherein M is at least one cation, n is the valence of the cation, y is between 4 and about 600, and z is between 0 and about 160. It is believed that the small gallium content of the sieves is at least in part incorporated in the crystalline lattice. Various attempts to remove the gallium from the gallosilicate sieves by exhaustive exchange with sodium, ammonium, and hydrogen ions were unsuccessful and therefore, the gallium content is considered nonexchangeable in the instant sieves.

TABLE 1

| d-Spacing Å (1) | Assigned Strength (2) | d-Spacing Å (1) | Assigned Strength (2) |
|---|---|---|---|
| 11.10 ± 0.20 | VS | 3.84 § 0.10 | MS |
| 9.96 ± 0.20 | MS | 3.71 § 0.10 | M |
| 6.34 ± 0.20 | W | 3.64 § 0.10 | W |
| 5.97 ± 0.20 | W | 2.98 § 0.10 | VW |
| 5.55 ± 0.20 | W | | |
| 4.25 ± 0.10 | VW | | |

(1) Copper K alpha radiation
(2) VW = very weak; W = weak; M = medium; MS = medium strong; VS = very strong The gallosilicate molecular sieve useful in this invention can be prepared by crystallizing an aqueous mixture, at a controlled pH, of a base, a gallium ion-affording material, an oxide of silicon, and an organic template compound.

Typically, the molar ratios of the various reactants can be varied to produce the crystalline gallosilicates of this invention. Specifically, the molar ratios of the initial reactant concentrations are indicated below:

| | Broad | Preferred | Most Preferred |
|---|---|---|---|
| $SiO_2/Ga_2O_3$ | 4–200 | 10–150 | 20–100 |
| Organic base/$SiO_2$ | 0.5–5 | 0.05–1 | 0.1–0.5 |
| $H_2O/SiO_2$ | 5–80 | 10–50 | 20–40 |
| Template/$SiO_2$ | 0–1 | 0.01–0.2 | 0.02–0.1 |

By regulation of the quantity of gallium (represented as $Ga_2O_3$) in the reaction mixture, it is possible to vary the $SiO_2/Ga_2O_3$ molar ratio in the final product. In general, it is desirable to have the gallium content of the gallosilicate sieve of this invention between about 0.1 and about 8 percent by weight of gallium. More preferably, he amount of gallium should be between about 0.2 and about 6 weight percent gallium and, most preferably, between about 0.3 and about 4 weight percent of gallium. Too much gallium in the reaction mixture appears to reduce the sieve crystallinity which reduces the catalytic usefulness of the sieve.

More specifically, the material useful in the present invention is prepared by mixing a base, a gallium ion-affording substance, an oxide of silicon, and an organic template compound in water (preferably distilled or deionized). The order of addition usually is not critical although a typical procedure is to dissolve the organic base and the gallium ion-affording substance in water and then add the template compound. Generally, the silicon oxide compound is added with mixing and the resulting slurry is transferred to a closed crystallization vessel for a suitable time. After crystallization, the resulting crystalline product can be filtered, washed with water, dried, and calcined.

During preparation, acidic conditions should be avoided. Advantageously, the pH of the reaction mixture falls within the range of about 9.0 to about 13.0; more preferably between about 10.0 and about 12.0 and most preferably between about 10.5 and 11.5.

Examples of oxides of silicon useful in this invention include silicic acid, sodium silicate, tetraalkyl silicates, and Ludox, a stabilized polymer of silicic acid manufactured by E. I. DuPont de Nemours & Co. Typically, the oxide of gallium source is a water-soluble gallium compound such as gallium nitrate or gallium acetate or another gallium compound, the anion of which is easily removed during sieve calcination prior to use. Water insoluble gallium compounds such as the oxide can be used as well.

Cations useful in the formation of the gallosilicate sieves include the sodium ion and the ammonium ion. The sieves also can be prepared directly in the hydrogen form with an organic base such as ethylenediamine.

The acidity of the gallosilicate sieves of this invention is high as measured by the Hammett $H_o$ function which lies in the neighborhood of about −3 to about −6.

Organic templates useful in preparing the crystalline gallosilicate include alkylammonium cations or precursors thereof such as tetraalkylammonium compounds, especially tetra-n-propylammonium compounds. A useful organic template is tetra-n-propylammonium bromide. Diamines, such as hexamethylenediamine, can be used.

The crystalline gallosilicate molecular sieve can be prepared by crystallizing a mixture of sources for an oxide of silicon, an oxide of gallium, an alkylammonium compound, and a base such as sodium hydroxide, ammonium hydroxide or ethylenediamine such that the initial reactant molar ratios of water to silica range from about 5 to about 80, preferably from about 10 to about 50 and most preferably from about 20 to about 40. In addition, preferable molar ratios for initial reactant silica to oxide of gallium range from about 4 to about 200, more preferably from about 10 to about 150 and most preferably from about 20 to about 100. The molar ratio of base to silicon oxide should be about above about 0.5, typically below about 5, preferably between about 0.05 and about 1.0 and most preferably between about 0.1 and about 0.5. The molar ratio of aklylammonium compound, such as tetra-n-propylammonium bromide, to silicon oxide can range from 0 to about 1 or above, typically above about 0.005, about 0.01 to about 0.2, most preferably about 0.02 to about 0.1.

The resulting slurry is transferred to a closed crystallization vessel and reacted usually at a pressure at least the vapor pressure of water for a time sufficient to permit crystallization which usually is about 0.25 to about 25 days, typically is about one to about ten days and preferably is about one to about seven days, at a temperature ranging from about 100° to about 250° C., preferably about 125° to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about three to about seven days. Samples of material can be removed during crystallization to check the degree of crystallization and determine the optimum crystallization time.

The crystalline material formed can be separated and recovered by well-known means such as filtration with aqueous washing. This material can be mildly dried for anywhere from a few hours to a few days at varying temperatures, typically about 50° to about 225° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, the mildly dried product is calcined at temperatures ranging from about 260° to about 850° C. and preferably from about 425° to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 hours. The gallosilicate sieves thus made generally have a surface area greater than about 300 sq. meters per gram as measured by the BET procedure.

Although not required, it is preferred to employ the above-described gallosilicate molecular sieve combined, dispersed or otherwise intimately admixed with a matrix of at least one non-molecular sieve, porous refractory inorganic oxide matrix component, as the use of such a matrix component facilitates the provision of the ultimate catalyst in a shape or form well suited for process use. Useful matrix components include alumina, silica, silicaalumina, zirconia, titania, etc., and various combinations thereof. The matrix components also can contain various adjuvants such as phosphorus oxides, boron oxides, and/or halogens such as fluorine or chlorine. Usefully, the molecular sieve-matrix dispersion contains about 1 to about 99 wt%, preferably about 40 to about 90 wt% and most preferably about 45 to about 85 wt% of a sieve component based upon the sieve-matrix dispersion weight.

Methods for dispersing molecular sieve materials within a matrix component are well-known to persons skilled in the art and applicable with respect to the shape-selective molecular sieve materials employed according to the present invention. A preferred method is to blend the molecular sieve component, preferably in finely-divided form, in a sol, hydrosol or hydrogel of an inorganic oxide, and then add a gelling medium such as ammonium hydroxide to the blend, with stirring, to produce a gel. The resulting gel can be dried, shaped if desired, and calcined. Drying preferably is conducted in air at a temperature of about 80° to about 350° F. (about 27° to about 177° C.) for a period of several seconds to several hours. Calcination preferably is conducted by heating in air at about 800° to about 1,200° F. (about 427° to about 649° C.) for a period of time ranging from about ½ to about 16 hours.

Another suitable method for preparing a dispersion of the molecular sieve component in a porous refractory oxide matrix component is to dry blend particles of each, preferably in finely-divided form, and then shape the dispersion if desired.

Alternatively, the sieve and a suitable matrix material like alpha-alumina monohydrate such as Conoco Catapal SB Alumina can be slurried with a small amount of a dilute weak acid such as acetic acid, dried at a suitable temperature under about 200° C., preferably about 100° to about 150° C. and then calcined at between about 350° and about 700° C., more preferably between about 400° to about 650° C.

Silica-supported catalyst compositions can be made by dry mixing the gallosilicate sieve with a silica source such as Cab-0-Sil, adding water and stirring. The resulting solid is then dried below about 200° C. and finally calcined between about 350° C. and 700° C.

The Group VIII metal component of the catalyst employed according to the present invention can be present in elemental form, as oxides, as nitrate, as chlorides or as combinations thereof. The Group VIII metal component employed in the present invention is preferably platinum. While all Group VIII metals can be employed in the present invention, platinum is preferred because it is relatively inactive for hydrogenolysis which would result in undesirable increased yields of $C_1$ and $C_2$.

The Group VIII metal component content preferably ranges from about 0.01 to about 10 wt.%, calculated as a zero valent metal and being based on the total weight of the catalytic composite, with about 0.01 to about 5 wt.% being more preferred, with a range of 0.05 to 1.0 wt.% being most preferred. Higher levels of metals can be employed if desired, though the degree of improvement resulting therefrom typically is insufficient to justify the added cost of the metals.

Relative proportions of the sieve component and the Group VIII metal component are such that at least a catalytically effective amount of each is present. The Group VIII metal component of the catalyst employed according to this invention can be associated with the sieve component by impregnation of the sieve component, or the sieve component can be dispersed in a porous refractory inorganic oxide matrix, with one or more solutions of compounds of the platinum group metal component which compounds are convertible to oxides on calcination. It also is contemplated, however, to impregnate a porous refractory inorganic oxide matrix component with such solutions of the Group VIII metal component and then blend the sieve component with the resulting impregnation product. Accordingly, the present invention contemplates the use of catalysts in which the Group VIII metal component is deposed on the sieve component, on a sieve matrix component dispersion or on the matrix component of a sieve matrix component.

The mechanics of impregnating the sieve component, matrix component or matrix composite with solutions of compounds convertible to metal oxides on calcination are well-known to persons skilled in the art and generally involve forming solutions of appropriate compounds in suitable solvents, preferably water, and then contacting the sieve matrix component or sieve matrix dispersion with an amount or amounts of solution or solutions sufficient to deposit appropriate amounts of metal or metal salts onto the sieve or sieve matrix dispersion. Useful metal compounds convertible to oxides are well-known to persons skilled in the art and include various ammonium salts as well as metal acetates, nitrates, anhydrides, etc.

The catalyst composition in accordance with the present invention also comprises a Group IB metal component. This Group IB metal component can be incorporated into the catalyst in the same manner as described above regarding the Group VIII metal component. The Group IB metal component preferably ranges from 0.01 to 10 wt.% calculated as the zero valent metal and being based on the total weight of the catalytic composite, with about 0.01 to about 5 wt.% being more preferred and with a range of 0.01 to about 1.5 being most preferred. The preferred Group IB metal is copper.

In another embodiment of the present invention the Group VIII, Group IB metal and gallosilicate-containing catalyst also contains chloride. The addition of chloride to the catalyst serves to increase the conversion and selectivity of the process of the invention to aromatics. A convenient method of adding the chloride is to include a predetermined volume of a solution containing a predetermined concentration of hydrochloric acid in the impregnating solution used to incorporate the platinum metal component with the catalyst.

Alternatively, the chloride can also be added during the impregnation of the metal salt if the metal salt contains chloride, such as hydrogen hexachloroplatinate ($H_2PtCl_6 \cdot 6H_2O$). If the chloride content in the chloride-containing metal salt is not sufficiently high, additional chloride can be added by the addition of hydrochloric acid to the impregnating solution.

In the instant embodiment of the invention the catalyst broadly contains 0.1 to 10 wt.% chloride, rreferably 0.5 to 5 wt.% chloride, and most preferably 0.5 to 1.5 wt.% chloride based on the final catalyst weight.

Also contemplated within the purview of the present invention chloride can be incorporated into the catalyst by the addition of chloride-containing compounds to the feed stream such as carbon tetrachloride, hydrochloric acid in amounts such that the final catalyst contains the above-prescribed amount of chloride.

The above-described catalysts can be employed in any suitable form such as spheres, extrudates, pellets, or C-shaped or cloverleaf-shaped particles.

The process of the present invention is carried out under suitable operating conditions set out below in Table 3 under which the feed is contacted with the above-described catalyst. It is also contemplated that a portion of the unconverted effluent stream can be recycled to the feed after separation from the aromatic products.

TABLE 3

| Conditions | Broad | Preferred | Most Preferred |
|---|---|---|---|
| Temperature, °F. | 700–4000 | 800–1200 | 850–1150 |
| Total Pressure, psig | 0–500 | 0–300 | 1–100 |
| WHSV, h-1 | 0.1–100 | 0.1–40 | 0.1–20 |

The present invention is described in further detail in connection with the following examples, it being understood that the same are for purposes of illustration only and not limitation.

EXAMPLE 1

The present example serves to show the improvement afforded by adding a Group IB metal, in this case copper, to a Group VIII-containing gallosilicate catalyst.

In particular, a platinum/copper/gallosilicate containing catalyst was prepared and tested in accordance with the invention. This catalyst had an MFI or pentasil zeolite structure, a gallium to silicon molar ratio of 0.035, and was dispersed in Catapal alumina (alpha-alumina monohydrate) in accordance with a ratio of 60 wt.% sieve to 40 wt.% alumina. In particular the powders of the gallosilicate and alumina were mechanically mixed then blended with a 5% acetic acid solution to form a paste which was dried at 70° C. overnight and calcined at 1100° F. for 18 hours. The gallosilicate-alumina composition was comminuted and sieved to obtain particles in the mesh range of 10 to 45. The gallosilicate-alumina particles were then impregnated by the method of incipient wetness with an aqueous solution containing predetermined concentrations of tetraamine platinum (II) nitrate and copper nitrate to obtain 0.1 wt.% platinum and 0.075 wt.% copper thereon. The so-impregnated particles were then dried at 70° C. overnight and subsequently calcined at 1000° F. (538° C.) for 2 hours.

A platinum gallosilicate catalyst containing 0.1 wt.% platinum was prepared in the same manner described above except that the copper nitrate was excluded from the impregnating solution.

Each catalyst prior to a process test was pretreated in the reactor with a drying step comprising passing nitrogen over the catalyst at 1000° F. for 0.5 hour followed by a reduction step comprising passing hydrogen at 1000° F. for 1 hour. Each catalyst was then tested for propane aromatization in a continuous flow fixed bed single pass downflow reactor under the following conditions as set out in Table 4.

TABLE 4

| | |
|---|---|
| Temperature | 1000° F. |
| Reactor Pressure | 50 psig |
| Feed | 100% $C_3H_8$ |
| Weight hourly space velocity (WHSV) | 9.4 grams propane per gram catalyst per hour |

The results of each catalyst test run are set out below in Tables 5 and 6 for the platinum/copper/gallosilicate and the platinum/gallosilicate catalysts respectively.

TABLE 5

| Time-on-stream, hour | 1 | 2 | 3 | 4 |
|---|---|---|---|---|
| Conversion per pass, wt % | 42.4 | 39.8 | 42.5 | 37.8 |
| Hydrocarbon distribution, wt % | | | | |
| Methane | 3.0 | 2.5 | 3.0 | 2.3 |
| Ethane | 24.7 | 24.0 | 26.4 | 23.7 |
| $C_4+$ aliphatics | 20.0 | 25.7 | 22.3 | 27.7 |
| Benzene | 11.0 | 8.9 | 9.5 | 8.2 |
| Toluene | 26.5 | 24.3 | 24.8 | 23.6 |
| Xylenes (incl. ethylbenzene) | 12.8 | 12.5 | 12.0 | 12.4 |
| $C_9+$ aromatics | 2.0 | 2.1 | 2.0 | 2.1 |
| Selectivity to Aromatics, wt % | 52.3 | 47.8 | 48.3 | 46.3 |
| Yield of Aromatics, wt % | 22.2 | 19.0 | 20.5 | 17.5 |

| Time-on-stream, hour | 5 | 6 | 7 | 8 |
|---|---|---|---|---|
| Conversion per pass, wt % | 40.2 | 36.5 | 39.2 | 39.2 |
| Hydrocarbon distribution, wt % | | | | |
| Methane | 2.7 | 2.2 | 2.7 | 2.7 |
| Ethane | 25.1 | 23.4 | 26.1 | 26.1 |
| $C_4+$ aliphatics | 24.1 | 27.5 | 25.5 | 25.5 |
| Benzene | 9.6 | 8.5 | 8.6 | 8.6 |
| Toluene | 24.8 | 24.1 | 23.8 | 23.8 |
| Xylenes (incl. ethylbenzene) | 11.9 | 12.3 | 11.6 | 11.6 |
| $C_9+$ aromatics | 1.8 | 2.0 | 1.7 | 1.7 |
| Selectivity to Aromatics, wt % | 48.1 | 46.9 | 45.7 | 45.7 |
| Yield of Aromatics, wt % | 19.3 | 17.1 | 17.9 | 17.9 |

TABLE 6

| Time-on-stream, hour | 1 | 2 | 3 | 4 |
|---|---|---|---|---|
| Conversion per pass, wt % | 38.2 | 34.2 | 35.1 | 34.1 |
| Hydrocarbon distribution, wt % | | | | |
| Methane | 3.0 | 2.3 | 2.4 | 2.3 |
| Ethane | 25.5 | 23.4 | 24.6 | 24.7 |
| $C_4+$ aliphatics | 22.2 | 27.8 | 26.8 | 28.0 |
| Benzene | 9.8 | 8.0 | 7.9 | 7.5 |
| Toluene | 24.8 | 23.2 | 23.3 | 22.7 |
| Xylenes (incl. ethylbenzene) | 12.7 | 13.0 | 13.0 | 12.8 |
| $C_9+$ aromatics | 2.0 | 2.3 | 2.0 | 2.0 |
| Selectivity to Aromatics, wt % | 49.3 | 46.5 | 46.2 | 45.0 |
| Yield of Aromatics, wt % | 18.8 | 15.9 | 16.2 | 15.3 |

| Time-on-stream, hour | 5 | 6 | 7 | 8 |
|---|---|---|---|---|
| Conversion per pass, wt % | 37.5 | 37.3 | 36.5 | 36.0 |
| Hydrocarbon distribution, wt % | | | | |
| Methane | 2.8 | 2.4 | 2.5 | 2.4 |
| Ethane | 26.5 | 25.0 | 25.9 | 25.7 |
| $C_4+$ aliphatics | 24.8 | 25.8 | 27.9 | 28.3 |
| Benzene | 9.3 | 8.5 | 7.8 | 7.7 |
| Toluene | 23.6 | 23.9 | 22.1 | 22.2 |
| Xylenes (incl. ethylbenzene) | 11.2 | 12.5 | 11.9 | 12.5 |
| $C_9+$ aromatics | 1.8 | 1.9 | 1.9 | 1.2 |
| Selectivity to Aromatics, wt % | 45.9 | 46.8 | 43.7 | 43.6 |
| Yield of Aromatics, wt % | 17.2 | 17.5 | 16.0 | 15.7 |

As is evident from a comparison of Tables 5 and 6, the addition of copper to the platinum gallosilicate markedly increased the conversion per pass and in selectivity of the reaction to aromatics without affecting the undesirable selectivity for cracked products, i.e., $C_1$ and $C_2$ formation. It should particularly be noted that addition of 0.075 wt. % copper increased the conversion per pass from about 35.5 wt. % to about 40 wt. % and the aromatics selectivity from about 45.5 to about 47.5 wt. %.

EXAMPLE 2

The present Example serves to demonstrate the aspect of the invention wherein chloride is added to a Group VIII-Group IB-metal-gallosilicate catalyst.

Specifically a gallosilicate MFI zeolite having a gallium to silicon ratio of 0.035 was dispersed in Catapal alumina in a manner substantially as described in Example 1. The platinum, gold and chloride components were added to the gallosilicate-alumina particles by incipient wetness impregnation. The platinum precursor salt was hydrogen hexachloroplatinate ($H_2PtCl_6.H_2O$). The gold precursor salt was hydrogen tetrachloroaurate ($HAuCl_4.3H_2O$). Enough platinum salt and gold salt were added so as to yield 0.1 wt. % Pt and 1.0 wt. % Au in the final catalyst. The chloride in the platinum and gold salts added amounted to 0.9 wt. % based on the final catalyst weight. After impregnation, the catalyst particles were dried at 70° C. overnight in a vacuum oven followed by calcination at 1000° F. for 2 hours in a muffle furnace under air flow.

The following Table 7 sets out the conditions employed and the results obtained when the above catalyst was employed in the process of the invention.

TABLE 7

| | | | |
|---|---|---|---|
| Catalyst | Pt/Au/Ga-silicate/Cl | | |
| Temperature, °F. | 1000 | | |
| Reactor pressure, psig | 50 | | |
| Feed | 100% $C_3H_8$ | | |
| WHSV, g propane/g catalyst · h | 9.4 | | |

| Time-on-stream, H | 1 | 3 | 4 |
|---|---|---|---|
| Conversion, wt % | 50.9 | 48.7 | 47.4 |
| Hydrocarbon distribution, wt % | | | |
| $C_1$ | 5.1 | 5.6 | 5.6 |
| $C_2$ | 32.9 | 34.2 | 33.6 |
| $C_4+$ aliphatics | 8.7 | 9.5 | 9.6 |
| Benzene | 14.3 | 13.9 | 14.2 |
| Toluene | 27.2 | 24.3 | 25.6 |
| Xylenes (incl. ethyl benzene) | 9.7 | 10.3 | 9.4 |
| $C_9+$ aromatics | 2.1 | 2.2 | 2.0 |
| Selectivity to Aromatics, wt % | 53.3 | 50.7 | 51.2 |
| Yield of Aromatics, wt % | 27.1 | 24.7 | 24.3 |

A comparison of the results of Table 7 with those of Table 6 is instructive. The gold and chloride addition to the catalyst in accordance with the present invention clearly enhances the conversion and selectivity to aromatics.

What is claimed is:

1. A process for converting a gaseous hydrocarbon feed containing paraffinic hydrocarbons to aromatic hydrocarbons which comprises contacting the feed under conversion conditions with a catalyst composition comprising a gallosilicate molecular sieve having the x-ray diffraction lines of Table 1 of the specification, a Group VIII metal component, and a Group IB metal component.

2. The process of claim 1 wherein the gaseous feed comprises $C_2$ through $C_5$ paraffins.

3. The process of claim 1 wherein the gaseous feed comprises propane.

4. The process of claim 1 wherein the Group VIII metal is present in an amount ranging from about 0.01 to about 10 wt % calculated as the zero valent metal and the Group IB metal is present in an amount ranging from about 0.01 to about 10 wt % calculated as the zero valent metal based on the total composition weight.

5. The process of claim 1 wherein the Group VIII metal is present in an amount ranging from about 0.01 to about 5 wt % calculated as the zero valent metal and the Group IB metal is present in an amount ranging from about 0.05 to about 5 wt % calculated as the zero valent metal based on the total composition weight.

6. The process of claim 1 wherein the Group VIII metal is present in an amount ranging from about 0.05 to about 1.0 wt % calculated as the zero valent metal and the Group IB metal is present in an amount ranging from about 0.01 to about 1.5 wt % calculated as the zero valent metal based on the total composition weight.

7. The process of claim 1 wherein the Group VIII metal is platinum.

8. The process of claim 1 wherein the Group IB metal is copper.

9. The process of claim 1 wherein the Group IB metal is gold.

10. The process of claim 1 wherein the Group VIII metal is platinum and the Group IB metal is copper.

11. The process of claim 1 wherein the Group VIII metal is platinum and the Group IB metal is gold.

12. The process of claim 1 wherein the gallosilicate molecular sieve is dispersed within a molecular sieve containing a porous refractory inorganic oxide matrix component.

13. The process of claim 12 wherein the refractory inorganic oxide component is selected from the group consisting of silica, silica-alumina, and alumina.

14. The process of claim 1 wherein the catalyst composition contains chloride in an amount ranging from about 0.1 to about 10 wt % based on the total weight of the composition.

15. The process of claim 1 wherein the hydrocarbon feed contains carbon tetrachloride in an amount such that the catalyst composition acquires about 0.1 to about 10 wt % chloride based on the total catalyst weight from the carbon tetrachloride in the feed.

16. The process of claim 13 wherein the gallosilicate molecular sieve is present in the dispersion such that the weight of the gallosilicate ranges from about 45 to about 85 wt % based on the total weight of the dispersion.

* * * * *